United States Patent
Klein et al.

(10) Patent No.: US 11,701,451 B1
(45) Date of Patent: Jul. 18, 2023

(54) SOFT TISSUE FILLER AND METHODS

(71) Applicant: Carbon Medical Technologies, Inc., St. Paul, MN (US)

(72) Inventors: Dean Allen Klein, North Oaks, MN (US); Eric A. Furlich, St. Louis Park, MN (US); Jared Klein, Minneapolis, MN (US)

(73) Assignee: Carbon Medical Technologies, Inc., St. Paul, MN (US)

( * ) Notice: Subject to any disclaimer, the term of this patent is extended or adjusted under 35 U.S.C. 154(b) by 0 days.

(21) Appl. No.: 17/692,594

(22) Filed: Mar. 11, 2022

(51) Int. Cl.
| | | |
|---|---|---|
| *A61L 27/26* | (2006.01) | |
| *A61K 9/00* | (2006.01) | |
| *A61K 31/716* | (2006.01) | |
| *A61K 31/729* | (2006.01) | |
| *A61L 27/20* | (2006.01) | |

(52) U.S. Cl.
CPC .......... *A61L 27/26* (2013.01); *A61K 9/0024* (2013.01); *A61K 31/716* (2013.01); *A61K 31/729* (2013.01); *A61L 27/20* (2013.01); *A61L 2430/34* (2013.01)

(58) Field of Classification Search
CPC ........ A61K 9/0024; A61K 31/716–729; A61L 27/20; A61L 27/26
See application file for complete search history.

(56) References Cited

U.S. PATENT DOCUMENTS

| | | | |
|---|---|---|---|
| 5,980,918 | A | 11/1999 | Klein |
| 6,168,799 | B1 | 1/2001 | Klein |
| 6,277,392 | B1 | 8/2001 | Klein |
| 6,394,965 | B1 | 5/2002 | Klein |
| 6,881,226 | B2 | 4/2005 | Corbitt, Jr. et al. |
| 8,231,894 | B2 | 7/2012 | Klein et al. |
| 8,592,574 | B2 | 11/2013 | Song et al. |
| 9,615,915 | B2 | 4/2017 | Lebovic et al. |
| 9,669,117 | B2 | 6/2017 | Campbell et al. |
| 9,980,809 | B2 | 5/2018 | Lebovic et al. |
| 10,022,475 | B2 | 7/2018 | Nguyen et al. |
| 10,413,381 | B2 | 9/2019 | Hermann et al. |
| 10,414,833 | B2 | 9/2019 | Lim et al. |
| 10,500,014 | B2 | 12/2019 | Hermann et al. |
| 2015/0335784 | A1 | 11/2015 | Barg |

OTHER PUBLICATIONS

Zhang, H. et al "Physically crosslinked hydrogels from polysaccharides . . . " React. Funct. Polym., vol. 73, pp. 923-928. (Year: 2013).*
Araujo, D. et al "Chitin-glucan compex hydrogels . . . " Polymers, vol. 14, pp. 1-17. (Year: 2022).*
Langenaeken, N. et al "Arabinoxylan, beta-glucan and pectin in barley . . . " The Plant J., vol. 103, pp. 1477-1489. (Year: 2020).*
Lee, S. et al "Artificial composed of gelatin . . . " Macromol. Res., vol. 11, No. 5, pp. 368-374. (Year: 2003).*
Agbenorhevi, J. et al "Rheological and microstructural investigation of oat b-glucan . . . " Int. J. Biol. Macromol., vol. 49, pp. 369-377. (Year: 2011).*

* cited by examiner

*Primary Examiner* — Leigh C Maier
(74) *Attorney, Agent, or Firm* — Robert C. Freed; Dykema Gossett PLLC

(57) ABSTRACT

A malleable polysaccharide soft tissue filler for filling tissue cavities or voids such as those resulting from tumor removal or other tissue resection. The soft tissue filler includes a first cross-linking polysaccharide, preferably a beta-D glucan and a second cross-linking polysaccharide. The soft tissue filler is both porous and malleable and can be formed to accommodate the tissue cavity or void. The soft tissue filler can include an embedded marker for locating on medical imaging. Methods of making the soft tissue filler including lyophilizing an aqueous polysaccharide suspension are disclosed. The second cross-linking polysaccharide provides for increased structural integrity in a high-porosity and malleable soft tissue filler in which the respective cross-linking polysaccharides synergistically provide structural scaffolding for one another. Methods of use are also disclosed.

19 Claims, 16 Drawing Sheets

| 51 | providing first powdered polysaccharide including beta-D glucan, second cross-linking polysaccharide, and water |
|---|---|
| 52 | mixing powdered polysaccharide with second cross-linking polysaccharide and water |
| 53 | providing mold in desired shape for soft tissue filler |
| 54 | transferring polysaccharide suspension into mold and lyophilizing in the mold to form a freeze-dried soft tissue filler of desired shape |
| 55 | removing lyophilized beta-glucan soft tissue filler from mold |

FIG. 7A

| 61 | providing first powdered polysaccharide including beta-D glucan, second cross-linking polysaccharide, and water |
|---|---|
| 62 | providing an imaging marker |
| 63 | mixing powdered polysaccharide with second cross-linking polysaccharide and water |
| 64 | providing mold in desired shape for soft tissue filler |
| 65 | transferring polysaccharide solution into mold and lyophilizing in the mold to form a freeze-dried soft tissue filler of desired shape |
| 66 | removing the lyophilized beta-glucan soft tissue filler from mold |
| 67 | inserting imaging marker into molded lyophilized beta-glucan soft tissue filler |

FIG. 7B

| | |
|---|---|
| 71 | evaluating size and shape of tissue cavity |
| 72 | choosing molded soft tissue filler including lyophilized beta-D glucan and second cross-linking polysaccharide of desired shape |
| 73 | forming the soft tissue filler as needed to approximate the shape of the tissue cavity to fill the tissue cavity and placing soft tissue filler in tissue cavity |
| 74 | closing surrounding tissue around the filled tissue cavity |

FIG. 8A

| | |
|---|---|
| 81 | evaluating size and shape of tissue cavity |
| 82 | choosing desired shape molded soft tissue filler including lyophilized beta-D glucan and second cross-linking polysaccharide of desired shape and embedded imaging marker |
| 83 | forming the soft tissue filler as needed to approximate the shape of the tissue cavity to fill the tissue cavity and placing soft tissue filler in tissue cavity |
| 84 | closing surrounding tissue around the filled tissue cavity |
| 85 | utilizing the embedded imaging marker to locate the filled tissue cavity using medical imaging |

FIG. 8B

| | |
|---|---|
| 91 | evaluating size and shape of tissue cavity |
| 92 | providing imaging marker |
| 93 | choosing desired shape molded soft tissue filler including lyophilized beta-D glucan and second cross-linking polysaccharide of desired shape |
| 94 | securing imaging marker to tissue adjacent to tissue cavity |
| 95 | forming the soft tissue filler as needed to approximate the shape of the tissue cavity to fill the tissue cavity and placing soft tissue filler in tissue cavity |
| 96 | closing surrounding tissue around the filled tissue cavity |
| 97 | utilizing imaging marker to locate the filled tissue cavity using medical imaging |

FIG. 8C

SOFT TISSUE FILLER AND METHODS

CROSS-REFERENCE TO RELATED APPLICATIONS

None.

FIELD OF THE INVENTION

The present invention relates to implantable prostheses designed to replace tissue removed for purposes of lumpectomy or the like, preferably devices for filling soft tissue cavities or voids following a surgical procedure that creates such a tissue cavity or void such as a lumpectomy, tumor removal, or other tissue resection procedure. The present invention also relates to methods of making a soft tissue filler, and methods of using a soft tissue filler.

DESCRIPTION OF THE RELATED ART

When soft tissue is removed, such as for lumpectomy, tumor removal, or other tissue resection or trauma, an empty space or surgical cavity or tissue void can be left where the tissue has been removed, and it is generally desirable to fill that empty space for proper healing, further treatment, or cosmesis. Various materials and methods have been used for this purpose, but there is continued need for improved materials, devices, and methods for filling such surgical cavities or tissue voids in soft tissue. It can be particularly desirable to fill the empty space with a material that allows native tissue ingrowth and healing, with eventual resorption or transformation of the material as native tissue grows in and replaces the removed tissue. Breast prostheses are utilized for augmentation mammoplasty and in cosmetic surgery. Prostheses also are indicated in breast cancer surgery, such as lumpectomies, where a portion of the breast is removed and can leave some disfigurement if not replaced by a similar amount of tissue and/or augmentation material. Similarly, biopsies can leave small dimples or imperfections if remedial steps are not taken. It is estimated that 287,000 new breast cancer patients are diagnosed each year, and it is believed that approximately two-thirds of those patients have a lumpectomy procedure performed to remove the cancerous tissue.

Other parties have made contributions to the efforts to address the need for tissue replacement devices and methods for addressing the same. U.S. Pat. Nos. 9,615,915 and 9,980,809 to Lebovic et al. disclose a device for placement in surgically created soft tissue spaces. The implantable device is reported to be bioabsorbable due to a somewhat rigid open framework that reportedly facilitates attachment of tissue thereto in a manner that is reported to help avoid post-surgical deformities. U.S. Pat. No. 8,592,574 to Song et al. disclose beta-glucan-based scaffold for biological tissue engineering using radiation fusion techniques. According to the production method of Song et. al. an aqueous solution of beta-glucan is reportedly cast and then irradiated to initiate a crosslinking reaction in such a way to form a gel or other solid scaffold, in the inventors' estimation, facilitating cell attachment, which reportedly making it possible to create a biomimetic environment conducive to the growth and differentiation of stem cells. Consequently, the inventors report that the beta-glucan scaffold of the invention can be usefully employed as a filler for voids in biological tissue and as scaffolding for reconstructive and corrective surgery. U.S. Pat. No. 6,881,226 to Corbitt, Jr. et al. disclose a breast implant having at least an outer shell which is composed of a resorbable material, preferably a collagen foam sized and shaped to replace excised tissue. The implant is reported to support surrounding tissue upon implantation, while allowing for in-growth of fibrous tissue to replace the implant. According to the inventors, various alternative embodiments provide an elastically compressible implant.

Accordingly, a need exists for implants and methods that can be adapted for replacement of small as well as large amounts of tissue. In addition, a need exists for tissue filler implants into which at least one imaging marker can be inserted such as a radiographic marker that can be visualized on medical imaging.

SUMMARY OF THE INVENTION

In a preferred embodiment, the present invention includes a soft tissue filler suitable for implantation into a living body as a tissue volume replacement to fill a surgical cavity or tissue void resulting from lumpectomy, tumor removal, or resulting from other tissue resection or trauma.

A preferred embodiment of the present invention provides a method of making a malleable soft tissue filler for use to fill a body cavity in the body of a mammal in which soft tissue has been removed to create the body cavity; the method of making a malleable soft tissue filler, comprising the steps of: 1) mixing from about 0.5 percent by weight to about 2 percent by weight of a first cross-linking polysaccharide material and from about 0.01 percent by weight to about 0.3 percent by weight of a second cross-linking polysaccharide material with water for a sufficient time to form an aqueous suspension of both the first cross-linking polysaccharide material and the second cross-linking polysaccharide material; wherein the first cross-linking polysaccharide material is a beta-D-glucan material and wherein the second cross-linking polysaccharide material is selected from the group consisting of chitin, chitosan, agarose, cellulose, pectin, xanthan gum, dextran, and hyaluronic acid; and 2) lyophilizing the aqueous suspension; wherein the step of lyophilizing the aqueous suspension preferably includes first freezing the aqueous suspension to form a frozen aqueous suspension and then desiccating the frozen aqueous suspension to make the malleable soft tissue filler; wherein the beta-D-glucan material is preferably selected from the group consisting of oat-derived (1-3), (1-4) beta-D glucan; yeast-derived (1-3),(1-6) beta-D-glucan; and mushroom-derived (1-3),(1-6) beta-D-glucan; and wherein the beta-D-glucan material is most preferably (1-3), (1-4) beta-D glucan; and the second cross-linking polysaccharide material is preferably agarose; and wherein the malleable soft tissue filler preferably includes from about 50.0 to about 99.9 percent by weight of the first cross-linking polysaccharide material and from about 0.03 percent by weight to about 50.0 percent by weight of a second cross-linking polysaccharide material and the density of the malleable soft tissue filler is from about 5.0 to about 300 mg/cubic centimeters (mg/cc).

A further preferred embodiment of the present invention provides a method of making a malleable soft tissue filler for use to fill a body cavity in the body of a mammal in which soft tissue has been removed to create the body cavity comprising the step of lyophilizing an aqueous suspension made by mixing from about 0.5 percent by weight to about 2 percent by weight of a first cross-linking polysaccharide material and from about 0.01 percent by weight to about 0.3 percent by weight of a second cross-linking polysaccharide material with water for a sufficient time to form an aqueous suspension of both the first cross-linking polysaccharide material and the second cross-linking polysaccharide material; wherein the first cross-linking polysaccharide material is a beta-D-glucan material and wherein the second cross-linking polysaccharide material is selected from the group consisting of chitin, chitosan, agarose, cellulose, pectin, xanthan gum, dextran and hyaluronic acid. In further preferred embodiments, the step of lyophilizing the aqueous suspension includes first freezing the aqueous suspension to form a frozen aqueous suspension and then desiccating the frozen aqueous suspension to make the malleable soft tissue filler; wherein the beta-D-glucan material is preferably (1-3), (1-4) beta-D glucan and the second cross-linking polysaccharide material is preferably agarose. In further embodiments the malleable soft tissue filler preferably has an open cell matrix and a density of from about 5.0 to about 300 mg/cc.

A further preferred embodiment of the present invention provides a malleable soft tissue filler made by a process, the process comprising the steps of 1) providing a first cross-linking polysaccharide material and a second cross-linking polysaccharide material and water; wherein the first cross-linking polysaccharide material is beta-D-glucan; 2) mixing a first portion of the first cross-linking polysaccharide material, a second portion of the second cross-linking polysaccharide material and a third portion of the water for a sufficient time to form an aqueous suspension; wherein the first portion of the first cross-linking polysaccharide material is from about 0.5 to about 2.0 percent by weight of the aqueous suspension and the second portion of the second cross-linking polysaccharide material is from about 0.01 to about 0.3 percent by weight of the aqueous suspension; and 3) lyophilizing the aqueous suspension; wherein the step of lyophilizing preferably includes freezing the aqueous suspension to form a frozen aqueous suspension and then desiccating the frozen aqueous suspension; wherein the first cross-linking polysaccharide material is preferably a (1-3), (1-4) beta-D-glucan material and wherein the second cross-linking polysaccharide material is preferably selected from the group consisting of chitin, chitosan, agarose, cellulose, pectin, xanthan gum, dextran, and hyaluronic acid; most preferably agarose.

A further preferred embodiment of the present invention provides a method of using a malleable soft tissue filler to fill a body cavity in a mammalian body in which soft tissue has been surgically removed from the body to create the body cavity; the method of using a malleable soft tissue filler to fill the body cavity preferably comprising: 1) providing a malleable soft tissue filler by lyophilizing an aqueous suspension made by mixing from about 0.5 percent by weight to about 2.0 percent by weight of a first cross-linking polysaccharide material and from about 0.01 percent by weight to about 0.3 percent by weight of a second cross-linking polysaccharide material with water for a sufficient time to form an aqueous suspension of both the first cross-linking polysaccharide material and the second cross-linking polysaccharide material; wherein the first cross-linking polysaccharide material is a beta-D-glucan material and wherein the second cross-linking polysaccharide material is selected from the group consisting of chitin, chitosan, agarose, cellulose, pectin, xanthan gum, dextran, and hyaluronic acid; wherein the step of lyophilizing the aqueous suspension preferably includes first freezing the aqueous suspension to form a frozen aqueous suspension and then desiccating the frozen aqueous suspension to make the malleable soft tissue filler; and 2) inserting the malleable soft tissue filler into the body cavity; and 3) closing the body cavity.

In preferred embodiments, the beta-D-glucan material is preferably (1-3), (1-4) beta-D glucan and the second cross-linking polysaccharide material is preferably agarose; and wherein the malleable soft tissue filler preferably includes from about 50.0 to about 99.9 percent by weight of the first cross-linking polysaccharide material and from about 0.03 percent by weight to about 50.0 percent by weight of a second cross-linking polysaccharide material and the density of the malleable soft tissue filler is from about 5.0 to about 300 mg/cubic centimeters (mg/cc).

A further preferred embodiment of the present invention provides a malleable soft tissue filler, comprising: from about 50.0 to about 99.9 percent by weight of a first cross-linking polysaccharide material and from about 0.03 percent by weight to about 50.0 percent by weight of a second cross-linking polysaccharide material; wherein the density of the malleable soft tissue filler is from about 5.0 to about 300 mg/cubic centimeters (mg/cc); wherein the first cross-linking polysaccharide material is a beta-D-glucan material and wherein the second cross-linking polysaccharide material is selected from the group consisting of chitin, chitosan, agarose, cellulose, pectin, xanthan gum, dextran, and hyaluronic acid; wherein the beta-D-glucan material is preferably (1-3), (1-4) beta-D glucan and the second cross-linking polysaccharide material is preferably agarose; and wherein the malleable soft tissue filler preferably includes at least one marker that is distinguishable from surrounding body tissue using common medical imaging technologies.

In working with beta-D-glucan materials, the present inventors discovered that, when suspensions of low concentration beta-D-glucan material were lyophilized, the resulting lyophilized material often crumbled when handled. This was undesirable as low concentration lyophilized beta-D-glucan materials were believed to be desirable for soft tissue prostheses. Efforts to provide a second cross-linking polysaccharide in a small concentrations were developed and the inventors have discovered the unanticipated effect that a second cross-linking polysaccharide in small concentrations appears to work synergistically with the beta-D-glucan to build scaffolding to support the structure of lyophilized low concentration cross-linking polysaccharide suspensions to provide a more stable structure than similar lyophilized low concentration cross-linking polysaccharide suspensions having only a single cross-linking polysaccharide. For that reason, it is believed that providing a very small concentration of a second cross-linking polysaccharide to the larger amount of beta-D-glucan works synergistically to provide scaffolding to support the structure of lyophilized low concentration cross-linking polysaccharide suspensions.

These and various other advantages and features of novelty which characterize the present invention are pointed out with particularity in the claims annexed hereto and forming a part hereof. However, for a better understanding of the invention, its advantages and objects obtained by its use, reference should be made to the drawings which form a further part hereof, and to the accompanying descriptive matter, in which there is illustrated and described preferred embodiments of the present invention.

BRIEF DESCRIPTION OF THE DRAWINGS

In the drawings, in which corresponding reference numerals and letters indicate corresponding parts of the various embodiments throughout the several views, and in which the various embodiments generally differ only in the manner described and/or shown, but otherwise include parts corresponding to the parts in the previously described embodiment;

FIG. 7A is a chart illustrating a method of method of making a malleable soft tissue filler of the present invention;

FIG. 7B is a chart illustrating a method of method of making a malleable soft tissue filler of the present invention, including an embedded imaging marker;

FIG. 8A is a chart illustrating a method of the present invention, for filling a tissue cavity or void utilizing a malleable soft tissue filler;

FIG. 8B is a chart illustrating a method of the present invention, for filling a tissue cavity or void utilizing a malleable soft tissue filler with an embedded imaging marker; and FIG. 8C is a chart illustrating a method of the present invention, for filling a tissue cavity or void utilizing a malleable soft tissue filler after securing external imaging marker(s) to tissue adjacent to the soft tissue filler.

DETAILED DESCRIPTION OF THE PREFERRED EMBODIMENTS

Figure 1:
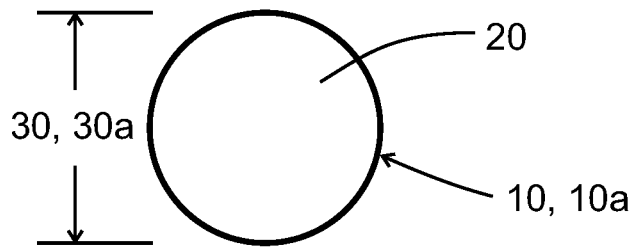
FIG. 1 is a schematic view illustrating a spherical soft tissue filler of the present invention.
Figure 2A:
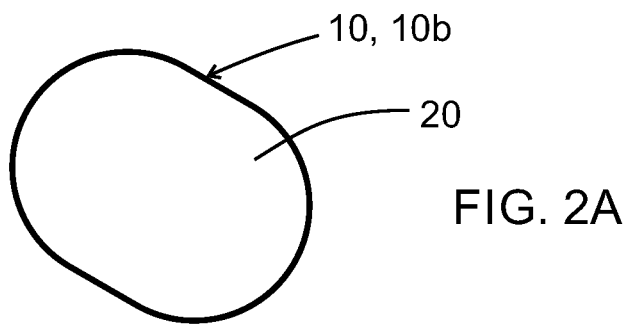
FIG. 2A is a perspective view schematically illustrating a capsular soft tissue filler of the present invention.
Figure 2B:
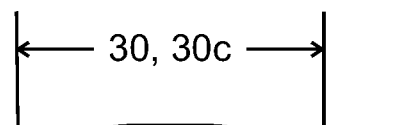
FIG. 2B is a top view of the capsular soft tissue filler of FIG. 2A.
Figure 2B:
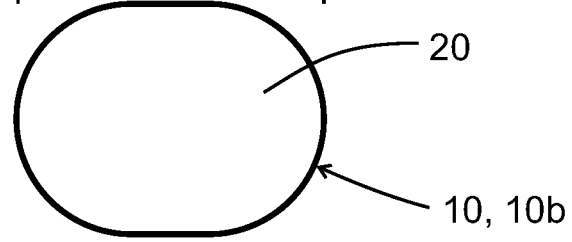
Figure 2C:
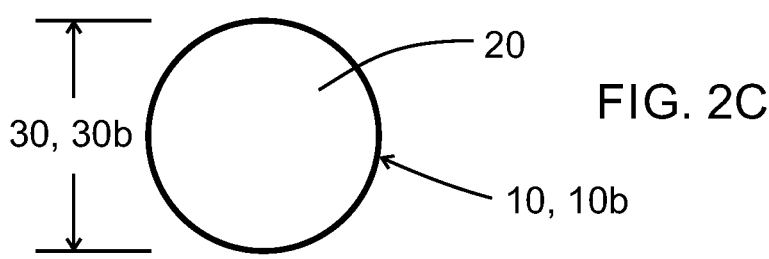
FIG. 2C is an end view of the capsular soft tissue filler of FIG. 2A.
Figure 2D:
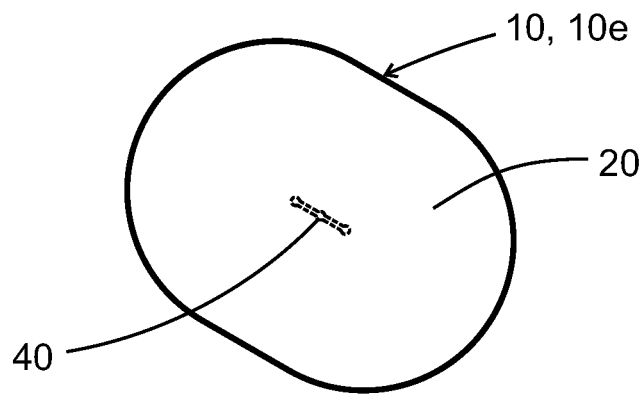
FIG. 2D is a perspective view of a capsular soft tissue filler including an embedded imaging marker.
Figure 2E:
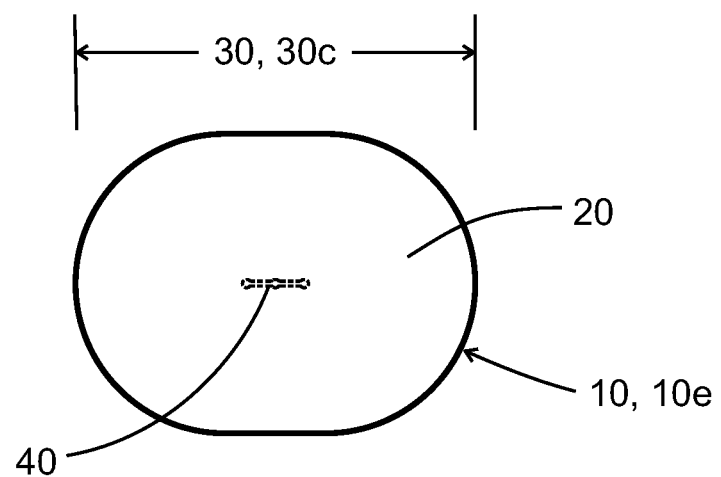
FIG. 2E is a top view of the capsular soft tissue filler of FIG. 2D.
Figure 2F:
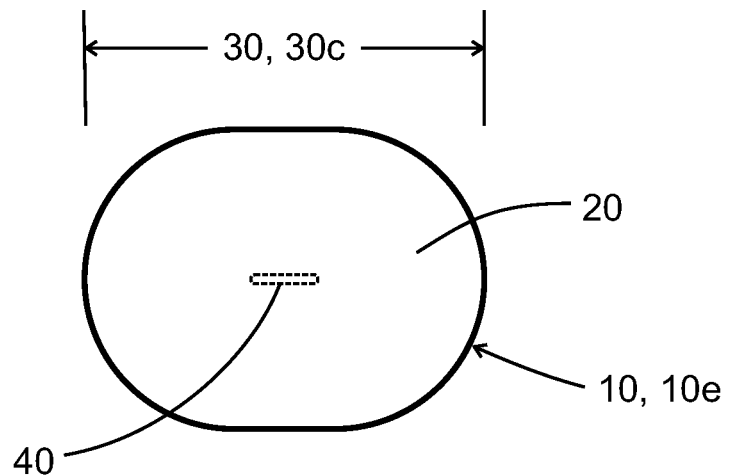
FIG. 2F is a side view of the capsular soft tissue filler of FIG. 2D.
Figure 2G:
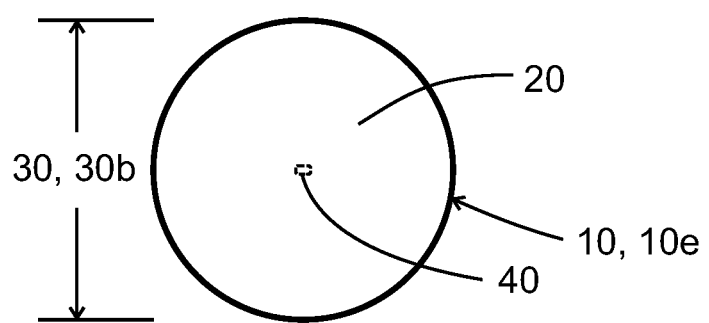
FIG. 2G is an end view of the capsular soft tissue filler of FIG. 2D.
Figure 3A:
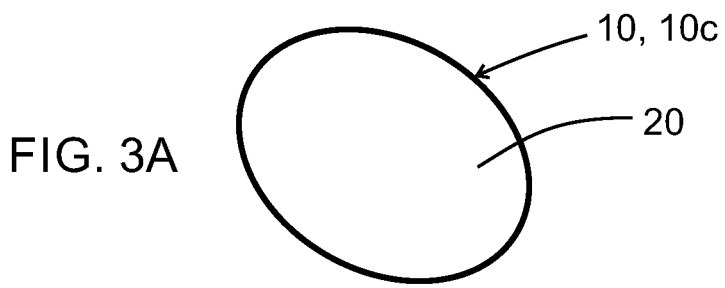
FIG. 3A is a perspective view schematically illustrating an ellipsoidal soft tissue filler of the present invention.
Figure 3B:
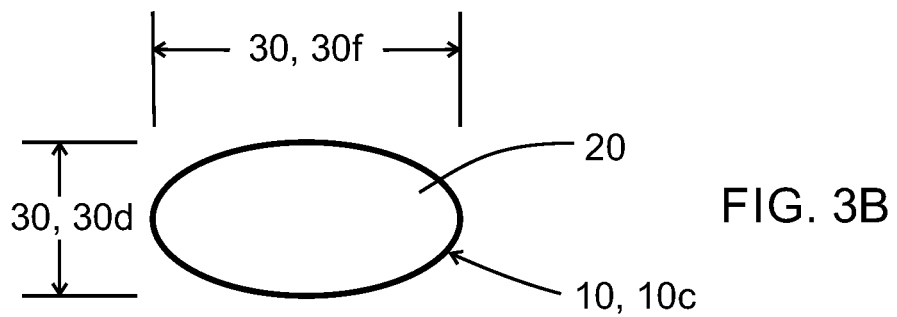
FIG. 3B is a top view of the ellipsoidal soft tissue filler of FIG. 3A.
Figure 3C:
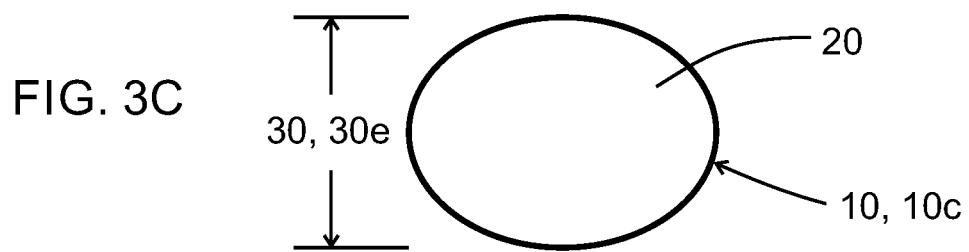
FIG. 3C is a side view of the ellipsoidal soft tissue filler of FIG. 3A.
Figure 3D:
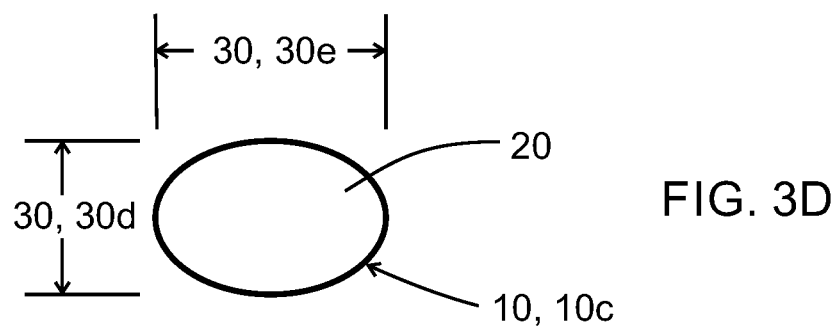
FIG. 3D is an end view of the ellipsoidal soft tissue filler of FIG. 3A.
Figure 3E:
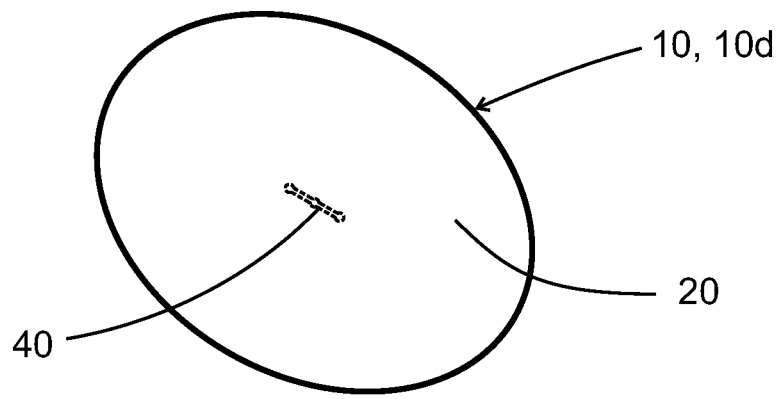
FIG. 3E is a perspective view of an ellipsoidal soft tissue filler including an embedded imaging marker.
Figure 3F:
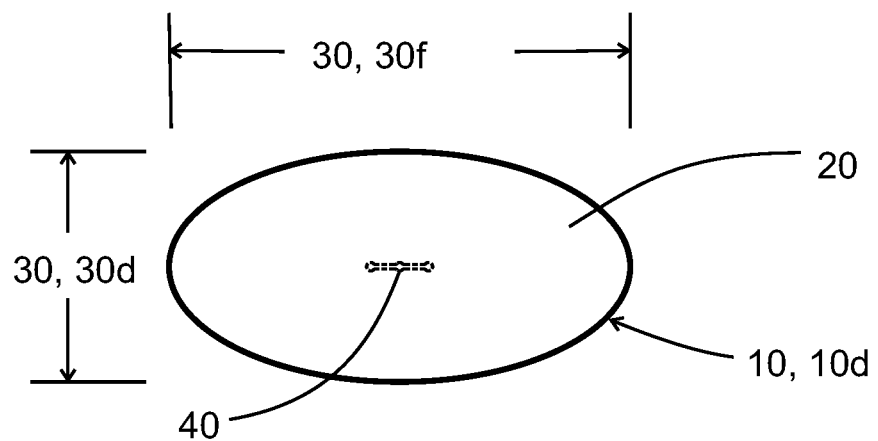
FIG. 3F is a top view of the ellipsoidal soft tissue filler of FIG. 3E.
Figure 3G:
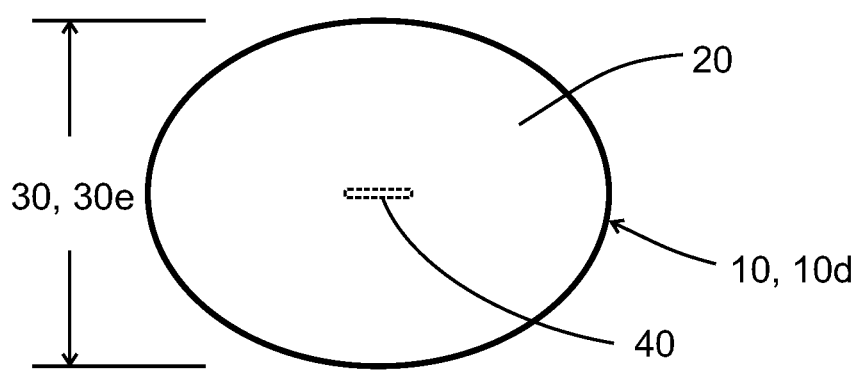
FIG. 3G is a side view of the ellipsoidal soft tissue filler of FIG. 3E.
Figure 3H:
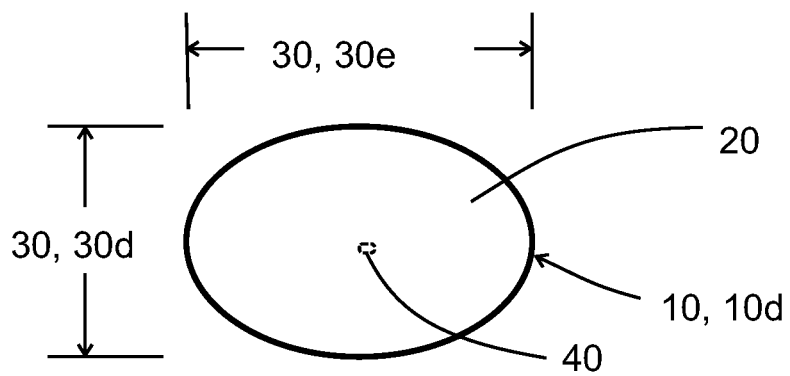
FIG. 3H is an end view of the ellipsoidal soft tissue filler of FIG. 3E.
Figure 4A:
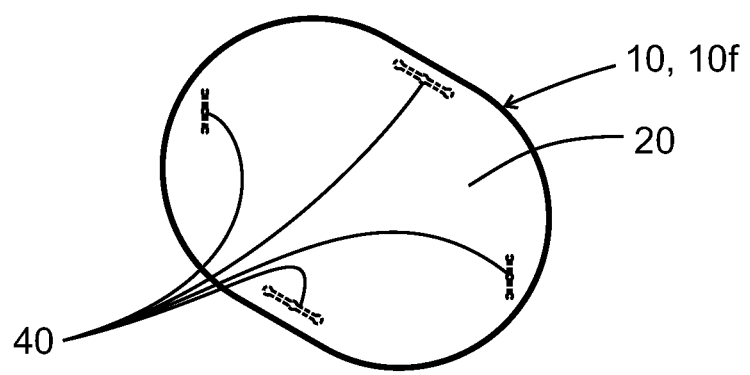
FIG. 4A is a perspective view of a capsular soft tissue filler including a plurality of embedded imaging markers.
Figure 4B:
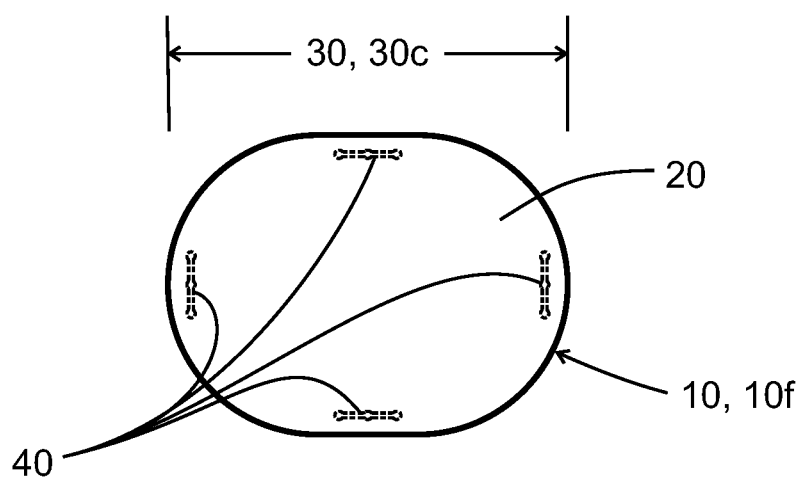
FIG. 4B is a top view of the capsular soft tissue filler of FIG. 4A.
Figure 4C:
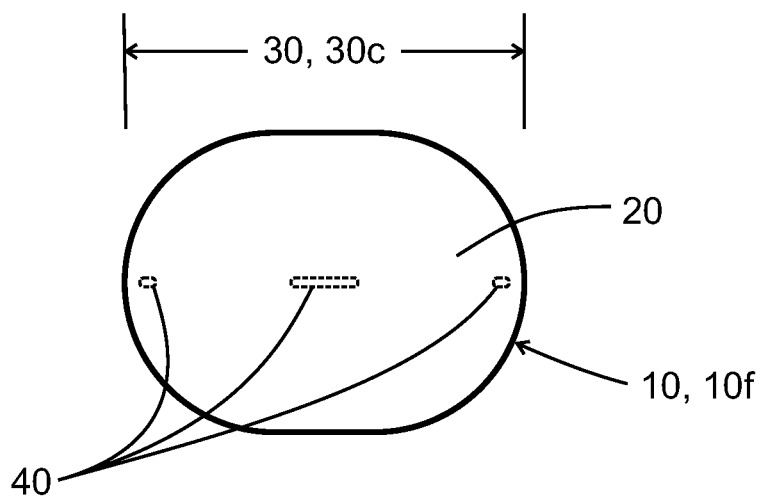
FIG. 4C is a side view of the capsular soft tissue filler of FIG. 4A.
Figure 4D:
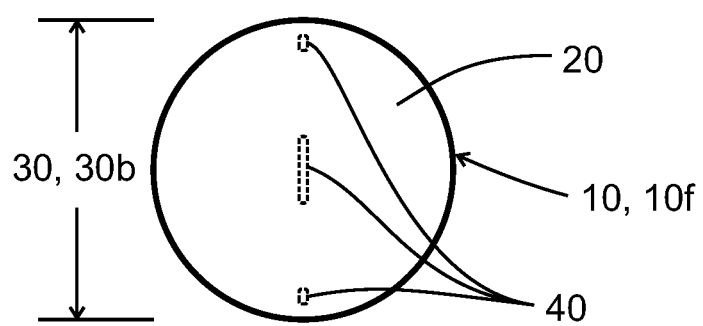
FIG. 4D is an end view of the capsular soft tissue filler of FIG. 4A.

Referring now to FIGS. 1-6D, the invention includes a soft tissue filler 10 suitable for implantation into a living body as tissue volume replacement to fill a surgical cavity or tissue void resulting from lumpectomy, tumor removal, or other tissue resection or trauma. In a preferred embodiment, the soft tissue filler 10 includes one or more pieces of malleable biocompatible filler material 20 including a first polysaccharide including beta-D-glucan and a second cross-linking polysaccharide; any moisture content of the malleable filler material 20 is preferably minimal. Preferably, the first polysaccharide beta-D-glucan includes (1-3), (1-4) beta-D glucan such as can be derived from oat endosperm. Preferred second cross-linking polysaccharides include chitin, chitosan, agarose, cellulose, pectin, xanthan gum, dextran, and hyaluronic acid. Preferably, the filler material 20 is configured as a porous matrix such as an open-cell matrix or foam structure as can be produced by lyophilizing a solution of the beta-D glucan and cross-linking polysaccharide material and is preferably supplied in various sizes and shapes to accommodate the surgical cavity or tissue void, and is malleable to allow a user to form a desired shape by primarily plastic deformation to accommodate the cavity or void. The filler material 20 is preferably supplied in various convex rounded shapes. For example, preferable shapes of soft tissue filler 10 include spherical soft tissue filler 10a, capsular soft tissue filler 10b, ellipsoidal soft tissue filler 10c. Other preferred soft tissue fillers 10 include ellipsoidal soft tissue filler with embedded imaging marker 10d, capsular soft tissue filler with embedded imaging marker 10e, capsular soft tissue filler with multiple embedded imaging markers 10f, capsular soft tissue filler with external imaging markers 10g, and capsular soft tissue filler with coupled imaging markers 10h. The filler material 20 is preferably supplied in sizes having various dimensions, diameters, axes, or extents 30 from about 0.5 cm to about 10 cm, although other sizes can be utilized as required to fill a particular tissue void. For example, preferable shapes include generally spherical shapes such as the spherical soft tissue filler 10a, including filler material 20 and having dimensions 30 including diameter 30a (FIG. 1). Various sizes of spherical soft tissue filler 10a can be utilized; preferably, the diameter 30a is from about 1 cm to about 4 cm. Other preferable shapes include capsular shapes having dimensions 30 including diameter 30b, preferably from about 2 cm to about 4 cm in diameter, and length 30c, preferably from about 3 cm to about 5 cm (FIGS. 2A-2G). More preferable capsular shapes have diameter 30b of about 3 cm, and length 30c of about 4 cm. Still other preferable shapes include ellipsoidal shapes having dimensions 30 including principal axes 30*d*, 30*e*, 30*f* varying from about 2 cm to about 5 cm (FIGS. 3A-3H). By careful preparation of the filler material 20, suitable malleability of the soft tissue filler 10 can be obtained for forming the piece(s) of filler material to accommodate the surgical cavity or tissue void. The porous structure of the filler material 20 facilitates tissue ingrowth and incorporation for enhanced stability of the soft tissue filler 10 with respect to the adjacent tissue.

The pieces of the filler material 20 are preferably highly porous, preferably including about 0.5% to about 8% polysaccharide and about 92% to about 99.5% air or pore space, and more preferably about 0.8% to about 2.0% polysaccharide and about 98% to about 99.2% pore space, and still more preferably about 1.0% to about 2.0% polysaccharide and about 98% to about 99% pore space. The pieces of the filler material 20 are preferably formed by lyophilization of a polysaccharide solution of similar concentrations; for example, about 1.5% polysaccharide in about 98.5% water, which after lyophilization would result in a piece of filler material 20 that is about 1.5% polysaccharide and about 98.5% pore space. The preferred drying process is lyophilization, also known as freeze-drying, desiccation, or cryodesiccation, which is a dehydration process accomplished by freezing the aqueous solution or suspension and lowering the pressure to remove the water, and produces a porous piece of filler material 20 that has sufficient structural integrity yet is still malleable so that it can be formed by a user to accommodate a soft tissue cavity or tissue void. Note that the solid vs. pore space, or amount of polysaccharide per bulk volume, may vary somewhat depending on the drying process. Note also that the processing of the oat material can leave a small amount of other materials present in the initial beta-D-glucan powder or solution so that up to about 10% of the weight can include other polysaccharides, ash, and other impurities. Preferably, a beta-D-glucan assay (such as can be obtained from Neogen Corp., Lansing, Mich.) is used to determine the actual amount of polysaccharide in a volume of soft tissue filler 10, and the amount of water in the solution is adjusted as needed to obtain the desired amount of polysaccharide vs. pore space. While other sources of beta-D-glucan can be utilized, oat-derived beta-D-glucan material is preferred due to the presently available purity.

The present inventors have discovered that filler material 20 having too little polysaccharide and too much pore space lacks sufficient structural integrity for optimal use as a soft tissue filler. It has also been discovered that filler material 20 having too much polysaccharide and too little pore space lacks sufficient malleability for optimal forming for use as a soft tissue filler. It has been further discovered that filler material 20 that includes two different polysaccharide materials, such as beta-D glucan and chitosan, or beta-D glucan and agarose, etc., can preferably provide greater material integrity and allow the use of pieces of filler material 20 having lower amounts of polysaccharide and higher amounts of pore space to be used. For example, porous lyophilized filler material 20 of 1.5% beta-D glucan alone is believed to lack the required structural integrity, but the addition of even a small amount of a different cross-linking polysaccharide such as those listed herein provides a synergistic effect, so that 1.0% beta-D glucan with 0.06% agarose, for example, produces a filler material 20 with sufficient structural integrity for use in filling soft tissue cavities or tissue voids.

In preferred embodiments, the filler material 20 preferably includes from about 50% to about 99.9% by weight of the first cross-linking polysaccharide material (for example, beta-D glucan) and from about 0.03% to about 50% percent by weight of the second cross-linking polysaccharide material (for example, chitin, chitosan, agarose, etc.). More preferably, filler material 20 includes from about 80% to about 98% by weight of the first cross-linking polysaccharide material and from about 0.05% to about 10% percent by weight of a second cross-linking polysaccharide material. The lyophilized filler material 20 is preferably highly porous, with the bulk density of the lyophilized filler material 20 preferably from about 5 mg/cm$^3$ to about 300 mg/cm$^3$, and more preferably from about 7.5 mg/cm$^3$ to about 250 mg/cm$^3$, and more preferably from about 10 mg/cm$^3$ to about 150 mg/cm$^3$, and yet more preferably from about 10 mg/cm$^3$ to about 25 mg/cm$^3$.

In other preferred embodiments, the soft tissue filler 10 includes at least one imaging marker 40 and is configured for use as a fiducial marker to accurately determine the location of a surgical cavity or tissue void after lumpectomy, tumor removal, or other tissue resection. More preferably, the soft tissue filler 10 includes at least one location marker or imaging marker, such as a radiographic marker, preferably a pyrolytic carbon-coated ceramic imaging marker 40 incorporated into lyophilized glucan gel carrier; still more preferably, the soft tissue filler includes at least one discrete pyrolytic carbon-coated zirconium oxide marker, such as the BiomarC® Enhanced Fiducial Marker (Carbon Medical Technologies, St. Paul, Minn.).

Preferably, the soft tissue filler is visible on medical imaging such as one or more of kV X-ray, CT, CBCT, mammography, ultrasound, and Magnetic Resonance Imaging (MRI). In one preferred example, the capsular soft tissue filler 10*e* includes an embedded imaging marker 40 (see FIGS. 2D-2G). In another preferred example, the ellipsoidal soft tissue filler 10*d* includes imaging marker 40 (see FIGS. 3E-H). In these examples, the imaging marker 40 is located at a desired location within the soft tissue filler 10*d*, 10*e*; the imaging marker 40 is preferably located near the center of the soft tissue filler 10*d*, 10*e*.

Note that in FIGS. 2D-2G and FIGS. 3E-5E, the markers 40 that are embedded in the soft tissue fillers 10 are indicated with dashed outlines, and the markers 40 that are external to the soft tissue fillers 10 are indicated with solid outlines; in FIGS. 6A-6D the markers 40 and the sleeves 44 are indicated with solid outlines to distinguish them from the adjacent spacers 46 for clarity of illustration, even though they are embedded within the soft tissue filler 10 and would be obscured by the filler material 20.

In further preferred examples, the capsular soft tissue filler 10*f* includes a plurality of imaging markers 40; in the example illustrated in FIGS. 4A-4D, the capsular soft tissue filler 10*f* includes 4 imaging markers 40 embedded within the capsular soft tissue filler 10*f*, distributed near the periphery of the capsular soft tissue filler 10*f*. By incorporating a plurality of imaging markers 40, the location of the margins of the filled tissue void can be effectively ascertained by medical imaging. The various example soft tissue fillers 10, including those illustrated herein, can include 1, 2, 3, 4, 5, 6, 7, 8, or more imaging markers 40.

Figure 5A:
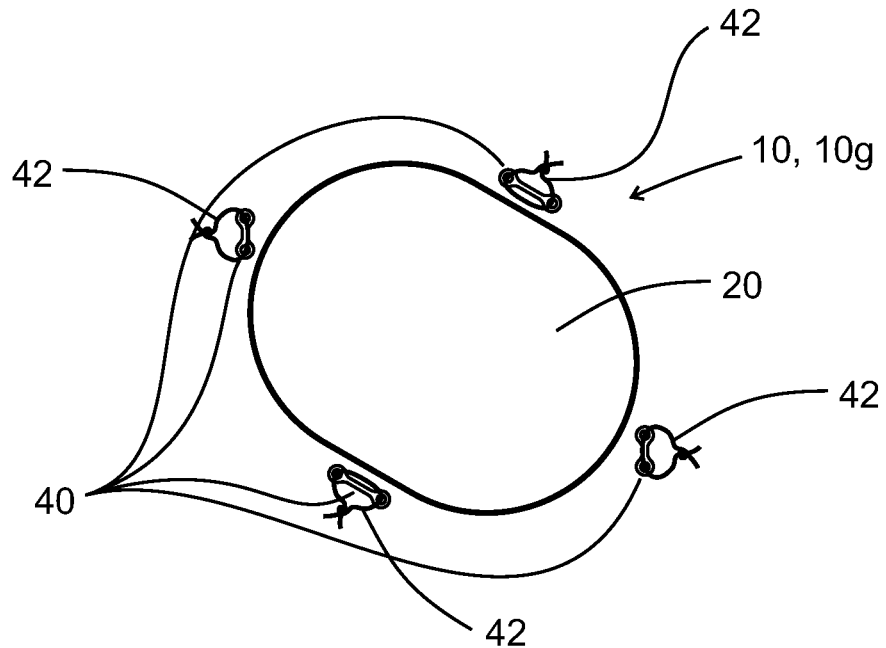
FIG. 5A is a schematic perspective view of a capsular soft tissue filler including a plurality of external imaging markers.
Figure 5B:
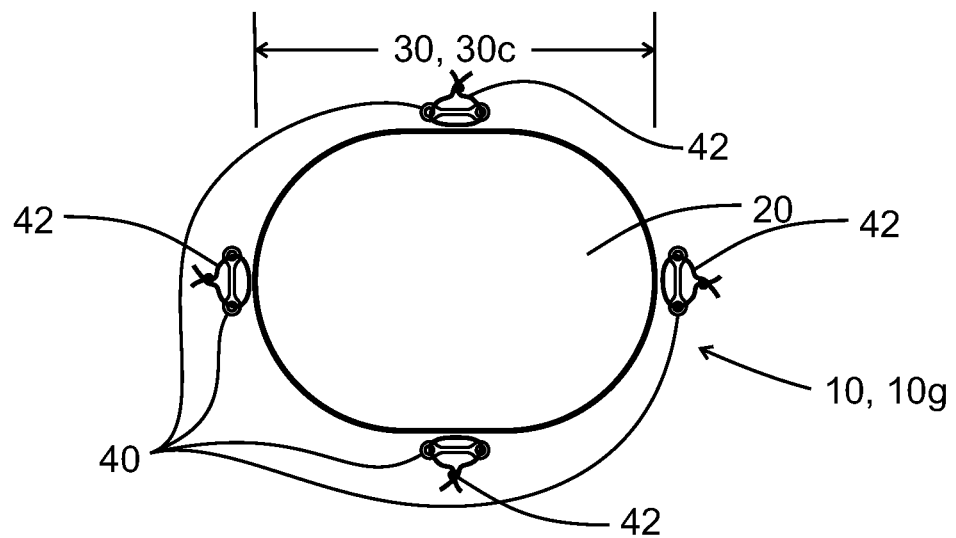
FIG. 5B is a top view of the capsular soft tissue filler of FIG. 5A.
Figure 5C:
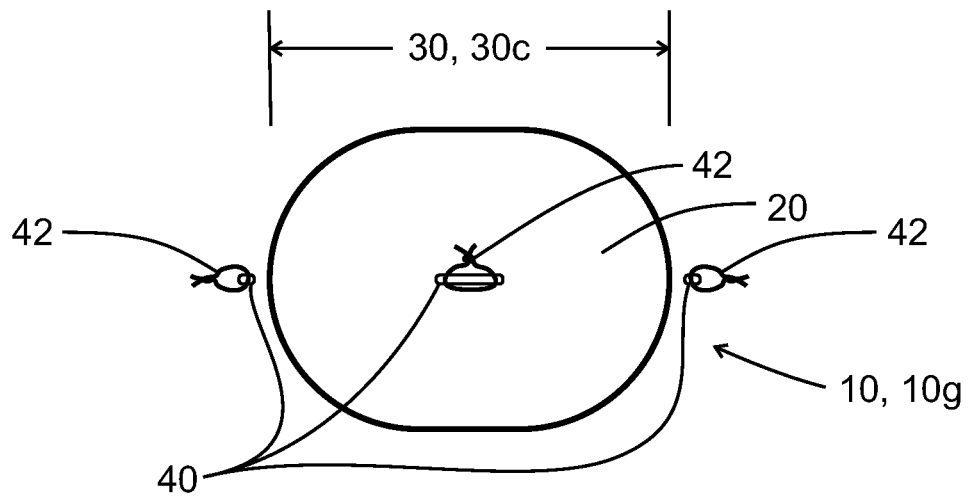
FIG. 5C is a side view of the capsular soft tissue filler of FIG. 5A.
Figure 5D:
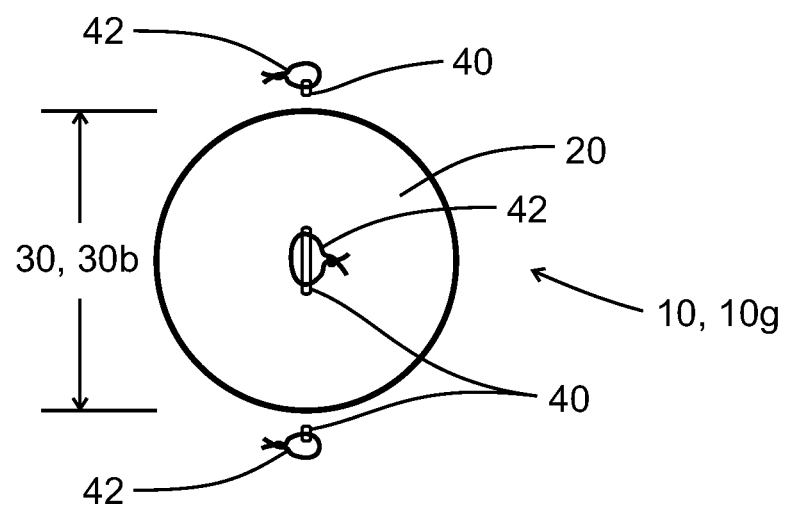
FIG. 5D is an end view of the capsular soft tissue filler of FIG. 5A.
Figure 5E:
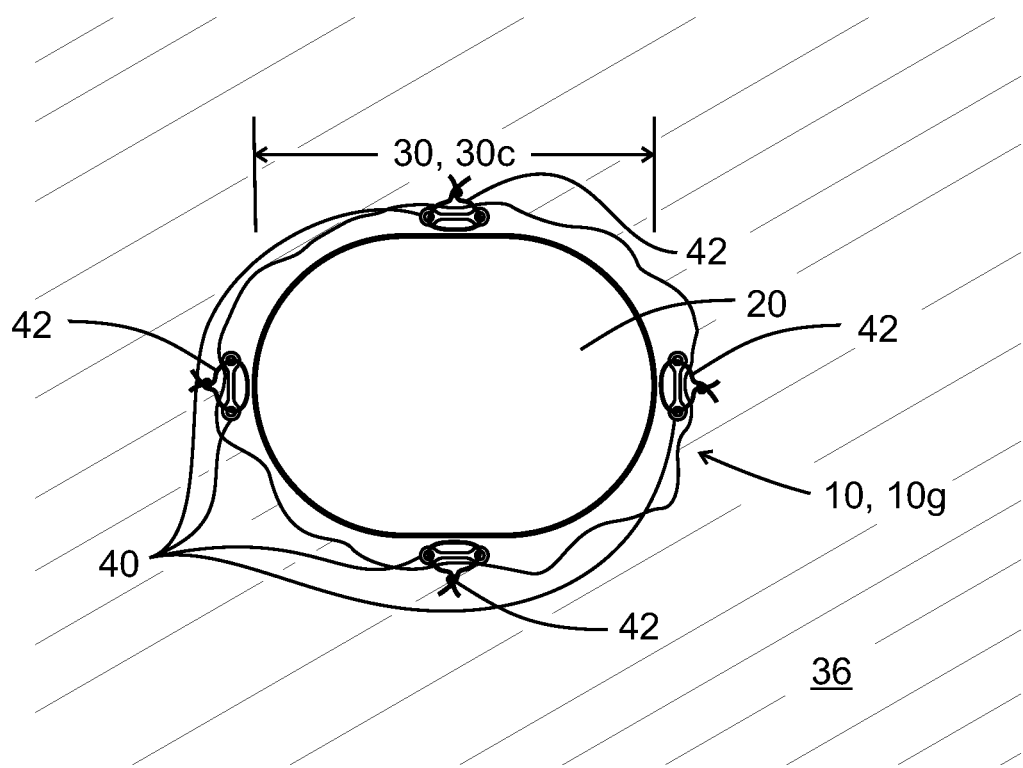
FIG. 5E is a schematic top view of the capsular soft tissue filler of FIG. 5A illustrating the capsular soft tissue filler in the tissue void, with the external imaging markers secured to the tissue adjacent to capsular soft tissue filler.
Figure 6A:
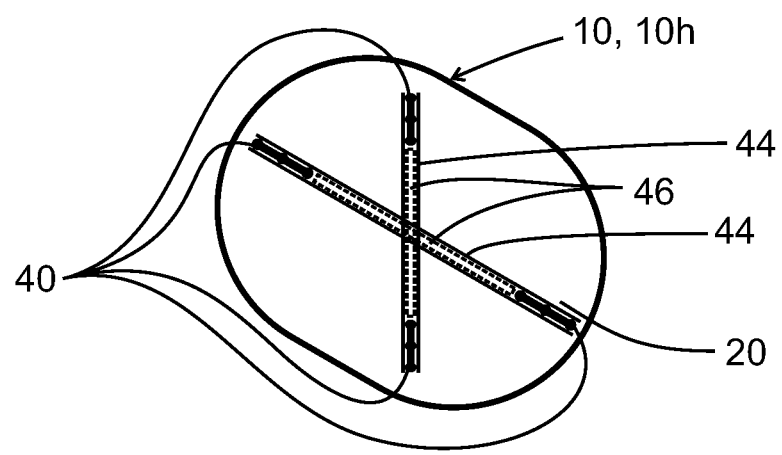
FIG. 6A is a perspective view of a capsular soft tissue filler including coupled imaging markers.
Figure 6B:
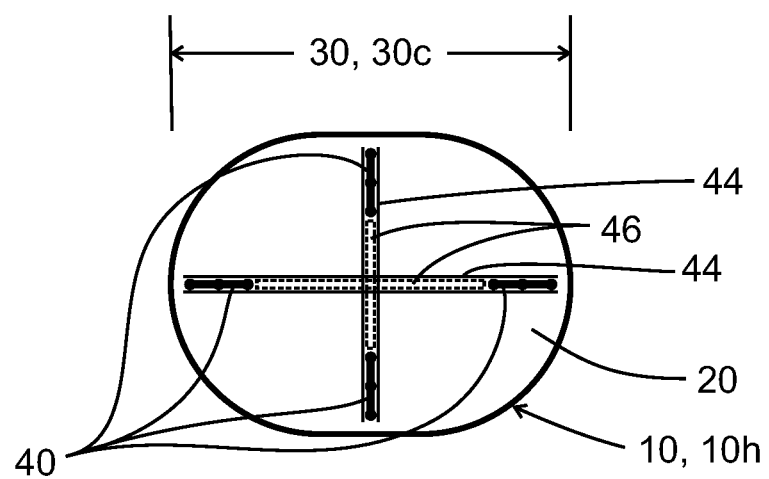
FIG. 6B is a top view of the capsular soft tissue filler of FIG. 6A.
Figure 6C:
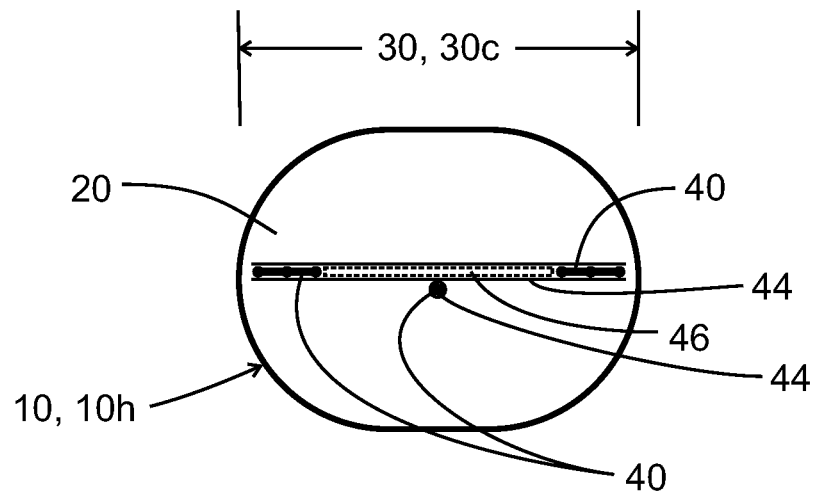
FIG. 6C is a side view of the capsular soft tissue filler of FIG. 6A.
Figure 6D:
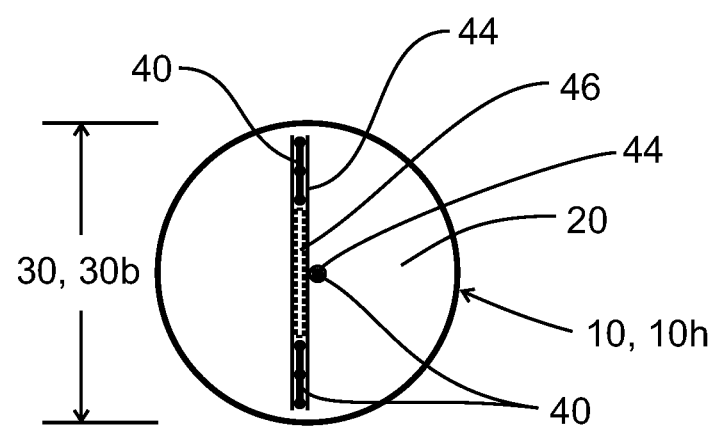
FIG. 6D is an end view of the capsular soft tissue filler of FIG. 6A.

In another preferred example, illustrated in FIGS. 5A-5E, the capsular soft tissue filler 10*g* includes a plurality of imaging markers 40 adjacent to the capsular soft tissue filler 10*g*. The plurality of imaging markers 40 are placed at the margins of the tissue void and preferably secured to the tissue 36; the capsular soft tissue filler 10*g* is placed to fill the tissue void. In FIG. 5E, the tissue 36 is indicated by fine hatching lines, and the imaging markers 40 are shown secured to the tissue 36 by sutures 42. Note that FIG. 5E is a schematic illustration showing a small gap between the tissue 36 and the soft tissue filler 10, 10*g* for clarity of illustration. After the imaging markers are secured by the sutures 42 and the soft tissue filler 10g is formed if needed to approximate the shape of the tissue void and the soft tissue filler 10g is placed in the tissue void, the tissue 36 is subsequently closed and the imaging markers 40 will generally be adjacent to the soft tissue filler 10g, with little or no gap. The margins of the filled tissue void can be located by use of the imaging markers 40 that are adjacent to the soft tissue filler 10g and are visible on medical imaging; the location of the margins of the filled tissue void can be determined at various times after placement of the soft tissue filler 10g and the imaging markers 40, such as for subsequent radiotherapy or other procedure. Various imaging markers 40 may be utilized in the present invention, preferably positioned at the margins of the tissue void or cavity, with the soft tissue filler 10 filling the tissue void or cavity. Preferably, the imaging marker(s) 40 are secured in position so that they remain at the margins of the tissue void for use as fiducial markers in medical imaging; more preferably, the imaging marker(s) 40 are secured to the tissue 36. Still more preferably, the imaging marker(s) 40 are secured to the tissue 36 by sutures 42.

In a still further preferred example, illustrated in FIGS. 6A-6D, the capsular soft tissue filler 10h includes coupled imaging markers 40 embedded within the capsular soft tissue filler 10h. In this example, two imaging markers 40 are arranged, one proximate each end of a sleeve 44, with a spacer 46 between the two imaging markers 40 to keep the imaging markers 40 separated. The spacer 46 is preferably a cylindrically-shaped polymer, and preferably keeps the imaging markers 40 separated so that the markers can be seen individually to aid in ascertaining the position of the soft tissue filler 10; for example, the spacer 46 may preferably keep the imaging markers 40 separated by about 10 mm. More preferably, the spacer keeps the imaging markers 40 separated so that the imaging markers 40 are located proximate opposed edges of the soft tissue filler 10h so that the location and extent of the filled tissue void or cavity can be determined upon medical imaging. In this example, two of these sleeves 44, each with a pair of imaging markers 40 separated by a spacer 46, are embedded within the capsular soft tissue filler 10h. Preferably, the sleeves are configured and arranged so that the imaging markers 40 provide useful location information upon medical imaging. In the example illustrated in FIGS. 6A-6D, two sleeves 44 are located near the center of the capsular soft tissue filler 10h and the two sleeves 44 are arranged perpendicular to each other. Note that in the drawings, the markers 40 and the sleeves 44 are indicated with solid lines for clarity, even though they may be embedded within the soft tissue filler 10h and may be obscured from view by the filler material 20.

Further configurations are anticipated, including soft tissue fillers 10 including at least one embedded imaging marker 40 and at least one adjacent imaging marker 40, for example. Further sizes and shapes of soft tissue fillers 10 can also be used, or more than one soft tissue filler 10 can be used in a particular application.

In a preferred method (see FIG. 7A), preparation of soft tissue filler 10 includes the step 51 of providing a first powdered polysaccharide, a second cross-linking polysaccharide, and water; the step 52 of mixing the provided first powdered polysaccharide with the second cross-linking polysaccharide and the water to form an aqueous polysaccharide suspension; the step 53 of providing a mold in a desired shape for the soft tissue filler 10; the step 54 of transferring the polysaccharide suspension into the provided mold and lyophilizing the polysaccharide suspension in the mold to form a porous dried soft tissue filler of the desired shape; and the step 55 of removing the lyophilized beta-D-glucan soft tissue filler from the mold. Note that herein, the inventors describe various polysaccharide mixtures in water as suspensions or as solutions; at some concentrations, the polysaccharides may dissolve in water and can therefore be described as aqueous solutions, and at other concentrations, the polysaccharides may not dissolve completely in water and therefore can be described as suspensions. Herein, the terms suspension and solution are used equivalently and encompass both scenarios.

In a preferred method, the step 51 of providing a first powdered polysaccharide includes providing a (1-3), (1-4) beta-D-glucan; in a more preferred method, the step 51 of providing a first powdered polysaccharide includes providing a (1-3), (1-4) beta-D-glucan derived from oats. The relative amounts of the beta-D-glucan, cross-linking polysaccharide, and water for the step 52 can be chosen to obtain desired stability, density and malleability properties of the resulting tissue filler. Preferably, the amount of cross-linking polysaccharide is about 3% to 9% by weight relative to the amount of beta-D-glucan powder; more preferably, the amount of cross-linking polysaccharide is about 6% by weight relative to the amount of beta-D-glucan powder. When mixed and dissolved in water prior to lyophilization, the amount of beta-D-glucan in the suspension is preferably from about 0.5 to about 3 wt. %, more preferably from about 0.5 to about 2.1 wt. %, and most preferably from about 0.5 to about 2.0%, and the amount of second cross-linking polysaccharide in the suspension is preferably from about 0.01 to about 0.5 wt. %, more preferably from about 0.015 to about 0.27 wt. %. In a preferred embodiment, the amount of beta-D-glucan in the suspension is from about 1.0 to about 2.0 wt. %, and the amount of the second cross-linking polysaccharide in solution is from about 0.03 to 0.19% by weight. The present inventors have used solutions of about 1.0%, 1.4%, and 1.8% beta-D-glucan by weight in water successfully to form a molded soft tissue filler 10 that has sufficient structural integrity yet is still malleable after lyophilization. The soft tissue filler 10 is preferably packaged sterile in impervious packaging that minimizes ingress of moisture and allows sterilization such as by gamma irradiation.

In a preferred method, the step 52 of mixing the provided first powdered polysaccharide, the second cross-linking polysaccharide, and the water includes heating the mixture. Preferably, the step 52 includes heating the mixture to from about 30 degrees Celsius to about 120 degrees Celsius. More preferably, the step 52 includes heating the mixture to from about 60 degrees Celsius to about 100 degrees Celsius. Still more preferably, the step 52 includes heating the mixture to from about 90 degrees Celsius to about 100 degrees Celsius. Heating the mixture to above 100 degrees Celsius may be accomplished under increased pressure.

In a preferred method (see FIG. 7B), the preparation of the soft tissue filler 10 includes the step 61 of providing a first powdered polysaccharide, a second cross-linking polysaccharide, and water; the step 62 of providing an imaging marker 40, which is preferably a pyrolytic carbon-coated ceramic imaging marker; the step 63 of mixing the provided first powdered polysaccharide with a cross-linking polysaccharide and suspending in water to form a polysaccharide suspension, preferably heating to about 90 C to 100 C, more preferably about 95 C; the step 64 of providing a mold in a desired shape for the soft tissue filler 10; the step 65 of transferring the polysaccharide solution into the provided mold and lyophilizing the polysaccharide solution in the mold to form a porous dried soft tissue filler of the desired shape; the step 66 of removing the lyophilized beta-D-glucan soft tissue filler from the mold; and the step 67 of preferably inserting the imaging marker 40 into the lyophilized beta-D-glucan soft tissue filler. In a preferred method, the step 61 of providing a first powdered polysaccharide includes providing a (1-3), (1-4) beta-D-glucan; in a more preferred method, the step 61 of providing a first powdered polysaccharide includes providing a (1-3), (1-4) beta-D-glucan derived from oats. The relative amounts of the beta-D-glucan, cross-linking polysaccharide, and water for the step 63 can be chosen to obtain desired stability, density and malleability properties of the resulting tissue filler. Preferably, the amount of cross-linking polysaccharide is about 3% to 9% by weight relative to the amount of beta-D-glucan powder; more preferably, the amount of cross-linking polysaccharide is about 6% by weight relative to the amount of beta-D-glucan powder. When mixed and dissolved in water prior to lyophilization, the amount of beta-D-glucan in the solution is preferably from about 0.5% to 3%, and the amount of cross-linking polysaccharide in solution is preferably from about 0.015% to 0.27% by weight; more preferably, the amount of beta-D-glucan in solution is about 1.0% to about 2.0%, and the amount of cross-linking polysaccharide in solution is from about 0.03% to 0.18% by weight. The inventors have used solutions of about 1.0%, 1.4%, and 1.8% beta-D-glucan by weight in water successfully to form a molded soft tissue filler 10 that has sufficient structural integrity yet is still malleable after lyophilization. The step 67 of inserting the imaging marker 40 into the lyophilized beta-D-glucan soft tissue filler is preferably accomplished by piercing the lyophilized beta-D-glucan soft tissue filler with a needle to create a pathway into the soft tissue filler material, inserting the imaging marker 40 into the pathway, and advancing the imaging marker 40 into the soft tissue filler material until it is about in the center of the soft tissue filler 10. The soft tissue filler 10 is preferably packaged sterile in impervious packaging that minimizes ingress of any moisture and allows sterilization such as by gamma irradiation.

In a preferred method, the step 63 of mixing the provided first powdered polysaccharide, the second cross-linking polysaccharide, and the water includes heating the mixture to a temperature above ambient temperature. Preferably, the step 63 includes heating the mixture to from about 30 degrees Celsius to about 120 degrees Celsius. More preferably, the step 63 includes heating the mixture to from about 60 degrees Celsius to about 100 degrees Celsius. Still more preferably, the step 63 includes heating the mixture to from about 90 degrees Celsius to about 100 degrees Celsius. Heating the mixture to above 100 degrees Celsius may be accomplished under increased pressure.

In some preferred embodiments, the step 51, 61 of providing a first powdered polysaccharide includes providing a 1% solution of oat-derived (1-3), (1-4) beta-D-glucan solution (such as Product #901-3045 available from Ceapro Inc., Alberta, Canada); adding ion exchange resin (such as Purolite UCW3700 mixed bed ion exchange resin, Purolite Corp., King of Prussia, PA) and stirring for 2 minutes to remove impurities from the solution, filtering to remove the resin, and adding sodium hydroxide as needed to adjust the solution to neutral pH; adding 95% ethyl alcohol and mixing for 5 minutes to precipitate the beta-D glucan and filtering to collect the flocculant; transferring the precipitate to a stainless steel pot and dissolving in water and stirring for 2 hours with heat to 70 C to blend and dissolve the precipitate; cooling the re-dissolved beta-D-glucan solution and adding 95% ethyl alcohol and mixing for 2 minutes to precipitate the beta-D-glucan and filtering in a 50 micron filter bag to collect the flocculant a second time; transferring the precipitate to an aluminum tray and breaking up the precipitate into small pieces and preferably mixing in a preservative such as benzalkonium chloride; loosely covering the pan with foil and freezing for 24 hours to evaporate any residual ethanol; freeze-drying or lyophilizing to remove any remaining moisture; milling to achieve a large-grain powder consistency. An assay of the resulting powder showed beta-D-glucan purity of 92% dry weight basis and a moisture content of 2%.

In a preferred embodiment (see FIG. 8A), a medical professional utilizes the soft tissue filler 10 to fill a tissue cavity or void according to a method that includes the step 71 of evaluating the size and shape of the surgical cavity or tissue void; the step 72 of choosing one or more soft tissue filler 10 pieces that closely approximates the size and shape of the cavity or void; the step 73 of forming the malleable soft tissue filler 10 and placing the soft tissue filler 10 in the tissue cavity so that the tissue cavity or void is filled with the soft tissue filler 10, mobilizing surrounding tissue as needed to create a smooth closure while minimizing any lumps or dimples when the surrounding tissue is closed around the soft tissue filler; and the step 74 of closing the surrounding tissue around the filled tissue cavity, ensuring that there is a layer of subcutaneous tissue covering the soft tissue filler 10. Preferably, the soft tissue filler 10 is chosen so that only minimal forming of the soft tissue filler 10 is required to approximate size and shape of the tissue cavity or void; more than one piece of soft tissue filler 10 may be used if required. The soft tissue filler material 20 of the soft tissue filler 10 is malleable, and will generally plastically deform; the porous structure of the soft tissue filler material 20 can be compressed as a user forms the soft tissue filler 10 to a desired shape.

In a preferred embodiment (see FIG. 8B), a medical professional utilizes the soft tissue filler 10 to fill a tissue cavity or void according to a method that includes the step 81 of evaluating the size and shape of the surgical cavity or tissue void; the step 82 of choosing one or more soft tissue filler 10 pieces that closely approximates the size and shape of the cavity or void and includes an imaging marker 40, preferably a pyrolytic carbon-coated ceramic imaging marker; the step 83 of forming the malleable soft tissue filler 10 as needed and placing the soft tissue filler 10 in the tissue cavity so that the tissue cavity or void is filled with the soft tissue filler 10, mobilizing surrounding tissue as needed to create a smooth closure while minimizing any lumps or dimples when the surrounding tissue is closed around the soft tissue filler; the step 84 of closing the surrounding tissue around the filled tissue cavity, ensuring that there is a layer of subcutaneous tissue covering the soft tissue filler 10; and the step 85 of utilizing the embedded imaging 40 to visualize the filled tissue cavity location using medical imaging. Preferably, the soft tissue filler 10 is chosen so that only minimal forming of the soft tissue filler 10 is required to approximate size and shape of the tissue cavity or void; more than one piece of soft tissue filler 10 may be used if required. The soft tissue filler material 20 of the soft tissue filler 10 is malleable, and will generally plastically deform; the porous structure of the soft tissue filler material 20 can be compressed as a user forms the soft tissue filler 10 to a desired shape. The step 85 of utilizing the embedded imaging marker 40 to visualize the filled tissue cavity location using medical imaging may be done at one or more times subsequent to initial placement of the soft tissue filler 10, and may be done by the same or one or more different medical professionals, using the imaging marker 40 as a fiducial marker such as to facilitate planning of subsequent surgical or radiotherapy procedures. For example, the imaging marker 40 can be utilized to mark a reference frame for stereotactic body radiotherapy and radiotherapy target localization.

In a preferred embodiment (see FIG. 8C), a medical professional utilizes the soft tissue filler 10 to fill a tissue cavity or void according to a method that includes the step 91 of evaluating the size and shape of the surgical cavity or tissue void; the step 92 of providing imaging marker(s) 40, preferably pyrolytic carbon-coated ceramic imaging marker(s); the step 93 of choosing one or more soft tissue filler 10 pieces that closely approximates the size and shape of the cavity or void; the step 94 of securing the imaging marker 40 to tissue adjacent the tissue cavity; the step 95 of forming the malleable soft tissue filler 10 as needed and placing the soft tissue filler 10 in the tissue cavity so that the tissue cavity or void is filled with the soft tissue filler 10, mobilizing surrounding tissue as needed to create a smooth closure while minimizing any lumps or dimples when the surrounding tissue is closed around the soft tissue filler, the step 96 of closing the surrounding tissue around the filled tissue cavity, ensuring that there is a layer of subcutaneous tissue covering the soft tissue filler 10; and the step 97 of utilizing the adjacent imaging marker 40 to visualize the filled tissue cavity location using medical imaging. Preferably, the soft tissue filler 10 is chosen so that only minimal forming of the soft tissue filler 10 is required to approximate size and shape of the tissue cavity or void; more than one piece of soft tissue filler 10 may be used if required. The soft tissue filler material 20 of the soft tissue filler 10 is malleable, and can plastically deform when formed by a user to better accommodate the shape of the tissue void or cavity to fill the cavity; the porous structure of the soft tissue filler material 20 can be compressed as a user forms the soft tissue filler 10 to a desired shape. Various imaging markers 40 can be utilized, and are preferably secured in position so that they can be used to determine the location of the tissue margin at the filled tissue cavity location. The step 97 of utilizing the imaging marker 40 to visualize the filled tissue cavity location using medical imaging may be done at one or more times subsequent to initial placement of the soft tissue filler 10, and may be done by the same or one or more different medical professionals, such as to use the imaging marker 40 as a fiducial marker to facilitate planning of subsequent surgical or radiotherapy procedures.

The location of the margins of the tissue void or cavity may need to be determined for various diagnostic or therapeutic purposes. Some medical imaging technologies may be able to visualize the location of the soft tissue filler 10, but preferably a plurality of imaging markers 40 are utilized that can be localized on medical imaging to facilitate locating the margins of the tissue void or cavity on medical imaging such as with kV X-ray, CT, CBCT, mammography, ultrasound, or Magnetic Resonance Imaging (MRI). Various imaging markers can be utilized for this purpose, including known imaging markers such as preferable pyrolytic carbon-coated ceramic markers.

The present inventors have made a variety of soft tissue fillers for evaluation, according to the present invention. Specific examples include the following.

Example 1a: Three 3 grams of Purolite UCW3700 mixed bed ion exchange resin was added to 30 kilograms of Ceapro Inc. Product #901-3045 1% solution of oat-derived (1-3), (1-4) beta-D-glucan solution and stirred for 2 minutes; the mixture was transferred to a 100 micron filter bag to remove the ion exchange resin, the pH of the filtered beta-D-glucan solution was adjusted to pH 7.0 by adding sodium hydroxide. 41 kilograms of 95% ethyl alcohol was added to 28.5 kilograms of the filtered beta-D-glucan solution and stirred under ventilation for 5 minutes to precipitate the beta-D glucan, and the flocculant was collected in a 50 micron filter bag. The precipitate was transferred to a stainless steel pot and 30 kilograms of reverse-osmosis purified water was added. The suspension was heated to 70 C, blended and stirred for 2 hours until the beta-D-glucan precipitate had dissolved into the water. The beta-D-glucan solution was cooled and then ladled into a container of 31 kilograms of 95% ethyl alcohol and stirred under ventilation for 2 minutes to precipitate the beta-D-glucan a second time and the flocculant was collected in a 50 micron filter bag. The precipitate was transferred to an aluminum tray and manually broken up the into small pieces. 200 parts per million benzalkonium chloride preservative was applied to the beta-D-glucan precipitate and thoroughly mixed; the aluminum tray was covered loosely with foil and placed in a freezer 24 hours to evaporate any residual ethanol. The evaporated beta-D-glucan was freeze-dried to remove any residual moisture, and then the solid beta-D-glucan was milled to achieve a large-grain powder consistency. 8.55 grams of Lonza Sea Kem Gold agarose was added. The powder was tested using a Neogen/Megazyme beta-D-glucan assay kit; the assay result indicated that the powder had a beta-D-glucan purity of 92% dry weight basis and a moisture content of 2%.

Example 1 b: 16 grams of purified beta-D-glucan powder (obtained from Example 1a) and 438 mg Lonza Sea Kem Gold agarose were mixed into 2059 milliliters of sterile water for injection. An immersion blender was used to break up any clumps and large globules, and the mixture was placed in a jacketed mixing vessel set to 95 C. The beta-D-glucan and agarose gel suspension was mixed for 4 hours until homogeneous and any dry clumps had been eliminated. An immersion blender was used to break up any clumps or globules at one-hour intervals. The suspension was cooled and transferred to an appropriate container. Analysis of the suspension showed 1.0% beta-D-glucan, pH 7.04, and viscosity 240 centipoise at 37 C.

Example 1 c: A syringe was used to transfer approximately 6 milliliters of the 1% beta-D-glucan suspension (obtained from Example 1b) to a 2 cm by 2 cm by 3 cm ellipsoid-shaped silicone ice mold. The mold was frozen on the shelf of a pilot freeze dryer. Temperature was normalized at OC for 45 minutes and the gradually decreased to −45 C over 165 minutes. The cover was removed from the elliptical mold and the beta-D-glucan was dried with a vacuum setpoint of 100 millitorr. The primary drying temperature was −10 C, and the secondary drying temperature was 25 C. The lyophilized beta-D-glucan gel was removed from the mold, and was a white solid structure maintaining the elliptical shape of the ice mold.

Example 2: 16 grams of purified beta-D-glucan powder (obtained from Example 1 a) and 438 mg Lonza Sea Kem Gold agarose were mixed into 1459 milliliters of sterile water for injection. An immersion blender was used to break up any clumps and large globules, and the mixture was placed in a jacketed mixing vessel set to 95 C. The beta-D-glucan and agarose gel suspension was mixed for 4 hours until homogeneous and any dry clumps had been eliminated. An immersion blender was used to break up any clumps or globules at one-hour intervals. The suspension was cooled and transferred to an appropriate container. Analysis of the suspension showed 1.74% beta-D-glucan, pH 6.96, and viscosity 1810 centipoise at 37 C. The beta-D-glucan suspension was transferred to a mold and lyophilized in the same manner as in Example 1c above, and the resulting molded structure was a white solid structure with greater density and structural rigidity compared to that of Example 1c.

Example 3: A syringe was used to transfer approximately 6 milliliters of the 1% beta-D-glucan suspension (obtained from Example 1b) to a 3 cm by 3 cm by 4 cm capsule-shaped aluminum and Teflon ice mold. The mold was frozen on the shelf of a pilot freeze dryer. Temperature was normalized at OC for 45 minutes and the gradually decreased to −45 C over 165 minutes. The cover was removed from the elliptical mold and the beta-D-glucan was dried with a vacuum setpoint of 100 millitorr. The primary drying temperature was −10 C, and the secondary drying temperature was 25 C. The lyophilized beta-D-glucan gel was removed from the mold, and was a white solid structure maintaining the shape of the ice mold.

Example 4: The lyophilized beta-D-glucan soft tissue filler (obtained from Example 3) was pierced with a needle to create a pathway into the soft tissue filler material, and a pyrolytic carbon-coated ceramic imaging marker (a BiomarC® Enhanced Fiducial Marker) was inserted into the pathway, and the imaging marker was advanced into the beta-D-glucan soft tissue filler until the imaging marker was about in the center of the soft tissue filler.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method of making a malleable soft tissue filler for use to fill a body cavity in the body of a mammal in which soft tissue has been removed to create the body cavity; the method of making a malleable soft tissue filler, comprising the steps of:
    creating a mixture by mixing from about 0.5 percent by weight to about 2 percent by weight of a first cross-linking polysaccharide material and from about 0.01 percent by weight to about 0.3 percent by weight of a second cross-linking polysaccharide material with water for a sufficient time to form an aqueous suspension of both the first cross-linking polysaccharide material and the second cross-linking polysaccharide material; wherein the first cross-linking polysaccharide material is (1-3), (1-4) beta-D-glucan and wherein the second cross-linking polysaccharide material is agarose; and
    lyophilizing the aqueous suspension.

2. The method of making a malleable soft tissue filler of claim 1, wherein the step of lyophilizing the aqueous suspension includes first freezing the aqueous suspension to form a frozen aqueous suspension and then desiccating the frozen aqueous suspension to make the malleable soft tissue filler.

3. The method of making a malleable soft tissue filler of claim 2, wherein the beta-D-glucan material is oat-derived (1-3),(1-4) beta-D-glucan.

4. The method of making a malleable soft tissue filler of claim 2; wherein the second cross-linking polysaccharide material is agarose.

5. The method of making a malleable soft tissue filler of claim 1; wherein the malleable soft tissue filler includes from about 50.0 to about 99.9 percent by weight of the first cross-linking polysaccharide material and from about 0.03 percent by weight to about 50.0 percent by weight of a second cross-linking polysaccharide material and the density of the malleable soft tissue filler is from about 5.0 to about 300 mg/cubic centimeters (mg/cc).

6. The method of making a malleable soft tissue filler of claim 1, wherein the step of mixing includes heating the mixture to a temperature from about 90 degrees Celsius to about 100 degrees Celsius.

7. A method of making a malleable soft tissue filler for use to fill a body cavity in the body of a mammal in which soft tissue has been removed to create the body cavity; the method of making a malleable soft tissue filler, comprising the step of:
    lyophilizing an aqueous suspension made by forming a mixture by mixing from about 0.5 percent by weight to about 2 percent by weight of a first cross-linking polysaccharide material and from about 0.01 percent by weight to about 0.3 percent by weight of a second cross-linking polysaccharide material with water for a sufficient time to form an aqueous suspension of both the first cross-linking polysaccharide material and the second cross-linking polysaccharide material; wherein the first cross-linking polysaccharide material is (1-3), (1-4) and wherein the second cross-linking polysaccharide material is agarose.

8. The method of making a malleable soft tissue filler of claim 7, wherein the step of lyophilizing the aqueous suspension includes first freezing the aqueous suspension to form a frozen aqueous suspension and then desiccating the frozen aqueous suspension to make the malleable soft tissue filler.

9. The method of making a malleable soft tissue filler of claim 8; wherein the malleable soft tissue filler has an open cell matrix and a density of from about 5.0 to about 300 mg/cc.

10. The method of making a malleable soft tissue filler of claim 7, wherein the step of forming a mixture includes heating the mixture to a temperature from about 90 degrees Celsius to about 100 degrees Celsius.

11. A malleable soft tissue filler made by a process, the process comprising the steps of:
    providing a first cross-linking polysaccharide material and a second cross-linking polysaccharide material and water; wherein the first cross-linking polysaccharide material is (1-3), (1-4) beta-D-glucan and the second cross-linking polysaccharide material is agarose;
    mixing a first portion of the first cross-linking polysaccharide material, a second portion of the second cross-linking polysaccharide material and a third portion of the water for a sufficient time to form a mixture; wherein the mixture is an aqueous suspension; wherein the first portion of the first cross-linking polysaccharide material is from about 0.5 to about 2 percent by weight of the aqueous suspension and the second portion of the second cross-linking polysaccharide material is from about 0.01 to about 0.3 percent by weight of the aqueous suspension; and
    lyophilizing the aqueous suspension.

12. The malleable soft tissue filler of claim 11, wherein the step of lyophilizing includes freezing the aqueous suspension to form a frozen aqueous suspension and then desiccating the frozen aqueous suspension.

13. The malleable soft tissue filler of claim 11, wherein the step of mixing includes heating the mixture to a temperature from about 90 degrees Celsius to about 100 degrees Celsius.

14. A method of using a malleable soft tissue filler to fill a body cavity in a mammalian body in which soft tissue has been surgically removed from the body to create the body cavity; the method of using a malleable soft tissue filler to fill the body cavity, comprising:
  providing a malleable soft tissue filler by lyophilizing an aqueous suspension made by creating a mixture by mixing from about 0.5 percent by weight to about 2.0 percent by weight of a first cross-linking polysaccharide material and from about 0.01 percent by weight to about 0.3 percent by weight of a second cross-linking polysaccharide material with water for a sufficient time to form an aqueous suspension of both the first cross-linking polysaccharide material and the second cross-linking polysaccharide material; wherein the first cross-linking polysaccharide material is (1-3), (1-4) beta-D-glucan and the second cross-linking polysaccharide material is agarose; wherein the step of lyophilizing the aqueous suspension includes first freezing the aqueous suspension to form a frozen aqueous suspension and then desiccating the frozen aqueous suspension to make the malleable soft tissue filler;
  inserting the malleable soft tissue filler into the body cavity; and
  closing the body cavity.

15. The method of using a malleable soft tissue filler of claim 14; wherein the malleable soft tissue filler includes from about 50.0 to about 99.9 percent by weight of the first cross-linking polysaccharide material and from about 0.03 percent by weight to about 50.0 percent by weight of a second cross-linking polysaccharide material and the density of the malleable soft tissue filler is from about 5.0 to about 300 mg/cubic centimeters (mg/cc).

16. The method of using a malleable soft tissue filler of claim 14, wherein the step of mixing includes heating the mixture to a temperature from about 90 degrees Celsius to about 100 degrees Celsius.

17. A malleable soft tissue filler, comprising: from about 50.0 to about 99.9 percent by weight of a first cross-linking polysaccharide material and from about 0.03 percent by weight to about 50.0 percent by weight of a second cross-linking polysaccharide material; wherein the density of the malleable soft tissue filler is from about 5.0 to about 300 mg/cubic centimeters (mg/cc); wherein the first cross-linking polysaccharide material is (1-3), (1-4) beta-D-glucan and the second cross-linking polysaccharide material is agarose.

18. The malleable soft tissue filler of claim 17, wherein the beta-D-glucan material is oat-derived (1-3), (1-4) beta-D-glucan.

19. The malleable soft tissue filler of claim 17, wherein the malleable soft tissue filler includes a at least one marker that is distinguishable from surrounding soft tissue using common medical imaging technologies.

* * * * *